United States Patent [19]

Alt et al.

[11] Patent Number: 4,846,880

[45] Date of Patent: Jul. 11, 1989

[54] 2-(DICHLOROACETYL)-3-SUBSTITUTED-1,2,3,4-TETRAHYDROISOQUINOLINES AS HERBICIDE ANTIDOTES

[75] Inventors: Gerhard H. Alt, University City; Harrison R. Hakes, Ballwin, both of Mo.

[73] Assignee: Monsanto Company, St. Louis, Mo.

[21] Appl. No.: 941,669

[22] Filed: Dec. 15, 1986

[51] Int. Cl.⁴ .............................................. A01N 43/42
[52] U.S. Cl. .......................................... 71/94; 71/93; 546/146
[58] Field of Search ....................................... 71/94, 93

[56] References Cited

U.S. PATENT DOCUMENTS 4,033,756  7/1977  Hoffman ................................. 71/94
4,208,203  6/1980  Hoffmann ............................... 71/95

OTHER PUBLICATIONS

Riebel, et al., "Chemical Abstracts", vol. 92, 1980, Col. 92:158971b.
Foery, et al., "Chemical Abstracts", vol. 105, 1986, Col. 105:166904j.

*Primary Examiner*—Richard L. Raymond
*Assistant Examiner*—James H. Turnipseed
*Attorney, Agent, or Firm*—J. Timothy Keane; William I. Andress

[57] ABSTRACT

2-(Dichloroacetyl)-3-substituted-1,2,3,4-tetrahydroisoquinoline compounds are antidotes for thiocarbamate, triazine-type and acetamide herbicides. These antidote compounds are especially effective in safening acetamide herbicides used to control grassy and broadleaf weeds in corn.

46 Claims, No Drawings

2-(DICHLOROACETYL)-3-SUBSTITUTED-1,2,3,4-TETRAHYDROISOQUINOLINES AS HERBICIDE ANTIDOTES

FIELD OF THE INVENTION

Herbicide antidotes are well-known crop protection chemicals. Of particular interest herein is a class of 2-(dichloroacetyl)-3-substituted-1,2,3,4-tetrahydroisoquinoline compounds found effective as antidotes for protecting crop plants from herbicide injury.

BACKGROUND OF THE INVENTION

Many herbicides injure crop plants at herbicide application rates necessary to control weed growth. Accordingly, many herbicides cannot be used for controlling weeds in the presence of certain crops. Uncontrolled weed growth, however, results in lower crop yield and reduced crop quality inasmuch as weeds compete with crops for light, water and soil nutrients. Reduction of herbicidal injury to crops without an unacceptable corresponding reduction of herbicidal action on the weeds can be accomplished by use of crop protectants known as herbicide "antidotes" or "safeners".

There are several known highly-phytotoxic acetanilide herbicides which provide excellent preemergent control of a broad spectrum of grassy and broadleaf weeds. Examples of three such acetanilides are acetochlor, 2-chloro-2'-methyl-6'-methoxy-N-(isopropoxymethyl) acetanilide, and 2-chloro-2'-methyl-6'-trifluoromethyl-N-(ethoxymethyl) acetanilide. Such acetanilide herbicides provide highly effective control of grassy and broadleaf weeds typically found in corn or sorghum crops, but at the cost of unacceptably high injury to the corn or sorghum crops. Because of excessive crop injury, general commercial use of these acetanilide herbicides in corn and grain sorghum has not been feasible, especially in soils containing less than about six percent organic matter.

There are several classes of quinoline-type compounds known as antidotes for herbicides. U.S. Pat. No. 4,033,756 to Hoffmann describes the compound N-dichloroacetyl-1,2,3,4-tetrahydroisoquinoline as an antidote for protecting the seed of corn, grain sorghum and rice, from injury by thiocarbamate herbicides, such as triallate, or acetamide herbicides such as alachlor. Bayer West German Application No. 28 28 222 describes this same compound, N-dichloroacetyl-1,2,3,4,-tetrahydroisoquinoline, as an antidote for protecting corn from a surface-applied pre-emergent treatment of a metazachlor-type herbicide. Bayer South African Pat. No. 79/3212 and counterpart Bayer Canadian Pat. No. 1,114,824 describe the compound N-dichloroacetyl-1,2,3,4-tetrahydroquinaldine as an antidote for protecting corn from a surface-applied pre-emergent treatment of a metazachlor-type herbicide. Bayer West German Application No. 29 30 450 describes the compound N-(α-chloropropionyl)-1,2,3,4-tetrahydroisoquinoline as an antidote for protecting corn from a surface-applied pre-emergent treatment of a metazachlor-type herbicide.

U.S. Pat. No. 4,137,070 to Pallos et al describes a large class of antidote compounds including the compound dichloroacetyl-2-methyldecahydroquinoline.

None of these publications mentions the three highly-phytotoxic acetanilides acetochlor, 2-chloro-2'-methyl-6'-methoxy-N-(isopropoxymethyl)acetanilide, or 2-chloro-2'-methyl-6'-trifluoromethyl-N-(ethoxymethyl)acetanilide.

Weed control for crops, especially corn crops, is one of the oldest and most highly developed areas in weed science. For a herbicide product to be accepted commercially for corn crops, such herbicide product must provide a relatively high level of control of both grassy and broadleaf weeds in corn, in addition to meeting several other criteria. For example, the herbicide must possess relatively high unit activity so that lower rates of herbicide application are feasible. Lower application rates are desirable in order to minimize exposure of the environment to the herbicide. At the same time, such herbicide must be selective in herbicidal effect so as not to injure corn crops. Herbicidal selectivity can be enhanced by use of an appropriate antidote in combination with the herbicide. But identification of an antidote having high safening activity suitable for a commercially-effective herbicide is a highly complicated task. Whether a compound or class of compounds provides efficacious antidote or safening activity is not a theoretical determination, but must be done empirically. Safening activity is determined empirically by observing the complex interaction of several biological and chemical factors, namely: the type of herbicide compound; the type of weed to be controlled; the type of crop to be protected from weed competition and herbicidal injury; the antidote compound itself; and the relative rates of application of the herbicide and antidote compounds required for effective weed control with low crop injury. Moreover, the herbicide and antidote must each possess chemical and physical properties enabling preparation of a stable formulation which is environmentally safe and easy to apply to the field.

DESCRIPTION OF THE INVENTION

A family of compounds useful as antidotes against hebicide injury to crops is provided by 2-(dichloroacetyl)-3-substituted-1,2,3,4-tetrahydoisoquinoline compounds embraced by the general structural formula

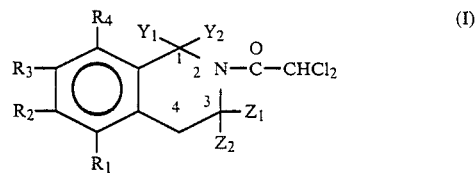

wherein each of $Y_1$, $Y_2$, $Z_1$, and $Z_2$ is independently selected from hydrido, alkyl and haloalkyl, with the proviso that at least one of $Z_1$ and $Z_2$ must be a group other than hydrido; and wherein each of $R_1$, $R_2$, $R_3$ and $R_4$ is independently selected from hydrido, alkyl, alkoxy and haloalkyl.

The term "2-(dichloroacetyl)-3-substituted-1,2,3,4-tetrahydroisoquinolines" is a general term to denote a class of compounds defined by Formula I. All compounds of this class are characterized in having at least one substituent, other than hydrido, at the three-position of the heterocyolic ring. All compounds of this class are further characterized in that the isoquinoline heterocyclic four-position carbon has two hydrido groups attached to it. Where the term "alkyl" is used, either alone or within another term such as "haloalkyl", the term "alkyl" embraces linear or branched radicals having one to ten carbon atoms. The term "haloalkyl"

embraces radicals wherein any one or more of the carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two bromo atoms, such as a dibromomethyl group, or two chloro atoms, such as a dichloromethyl group, or one bromo atom and one chloro atom, such as a bromochloromethyl group. Examples of a polyhaloalkyl are trifluoromethyl and perfluoroethyl groups. The term "alkoxy" embraces linear or branched oxy-containing alkyl radicals having one to ten carbon atoms, such as a methoxy group.

Also included in this invention are the stereo and optical isomers of compounds within the class defined by Formula I.

Preferred compounds within Formula I are 2-(dichloroacetyl)-3-substituted-1,2,3,4-tetrahydroisoquinolines wherein each of $Y_1$, $Y_2$, $Z_1$ and $Z_2$ is independently selected from hydrido, linear or branched alkyl groups of one to ten carbon atoms and perfluoroalkyl, and wherein each of $R_1$ through $R_4$ is independently selected from hydrido and linear or branched alkyl groups of one to ten carbon atoms, with at least one of $Z_1$ and $Z_2$ being a linear or branched alkyl group of one to ten carbon atoms.

Especially preferred antidote compounds are 2-(dichloroacetyl)-3-substituted-1,2,3,4-tetrahydroisoquinolines of Formula I wherein each of $Y_1$, $Y_2$, $Z_1$ and $Z_2$ is independently selected from hydrido, linear or branched alkyl groups of one to five carbon atoms and trifluoromethyl, and wherein each of $R_1$ through $R_4$ is hydrido, with either of $Z_1$ or $Z_2$ being a linear or branched alkyl group of one to five carbon atoms.

The isoquinoline compounds of Formula I are effective antidotes for several highly phytotoxic acetanilides especially where such acetanilides are used in corn for control of a greater variety of grassy and broadleaf weeds than typically provided by the commercial herbicide alachlor. Combinations which include at least one of these highly-phytotoxic acetanilide herbicides and an isoquinoline antidote compound of Formula I have been found to possess many advantages over alachlor for pre-emergent control of troublesome grassy and broadleaf weeds in corn and grain sorghum. For example, these acetanilides-isoquinoline combinations effectively control broadleaf weeds, such as velvetleaf and morningglory, and grassy weeds, such as barnyardgrass and green foxtail, while alachlor does not consistently control such weeds. Surprisingly, the isoquinoline antidotes of Formula I reduces injury to corn and sorghum due to the highly-phytotoxic acetanilides, without interfering with the efficacy of acetanilides as herbicides in these crops. In addition to broader spectrum weed control, these acetanilide herbicides, especially acetochlor, provide several other advantages over alachlor, namely, higher unit activity, lower application rates in most soils and higher activity in high organic matter soils. For example, for those weeds controlled effectively by both acetochlor and alachlor, acetochlor provides equivalent weed control at about one-half the application rate of alachlor. This lower effective application rate for acetochlor translates into substantially lower exposure of the environment to the herbicide. By use of one of the isoquinoline antidotes of Formula I in combination with acetochlor, all of these advantages of acetochlor are available to improve crop production at a lower unit cost.

A class of highly-phytotoxic acetanilides, which can be safened by the described isoquinoline antidote compounds, is defined by general Formula II:

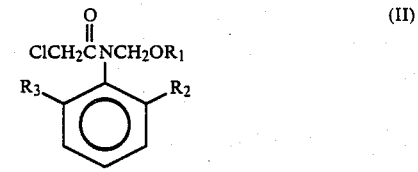

wherein $R_1$ is a linear or branched alkyl group of one to ten carbon atoms; and wherein each of $R_2$ and $R_3$ is independently selected from hydrido, linear or branched alkyl groups of one to ten carbon atoms, alkoxy having a linear or branched alkyl portion of one to ten carbon atoms, alkoxyalkyl having one or more oxy groups connected to a linear or branched alkyl portions of one to ten carbon atoms, haloalkyl having a linear or branched alkyl portion of one to ten carbon atoms substituted with one or more halo groups selected from iodo, bromo, chloro and fluoro, with the proviso that when $R_2$ is ethyl and $R_3$ is ethyl, then $R_1$ cannot be methyl.

Preferred herbicide compounds of Formula II are those wherein $R_1$ is a linear or branched alkyl group of one to five carbon atom, wherein each of $R_2$ and $R_3$ is independently selected from linear or branched alkyl groups of one to five carbon atoms, alkoxy groups having linear or branched portions of one to five carbon atoms, and perfluoroalkyl groups having branched or linear alkyl portions of one to five carbon atoms.

Especially preferred herbicide compounds within Formula II are those embraced by Formula III:

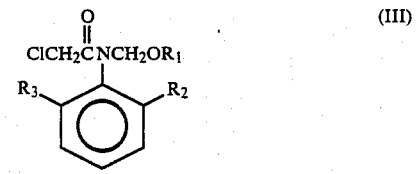

wherein $R_1$ is selected from methyl, ethyl, n-propyl, isopropyl, n-butyl, isobutyl, sec-butyl and tert-butyl; $R_2$ is selected from methyl, ethyl, methoxy, ethoxy, and trifluoromethyl groups; and $R_3$ is selected from methyl or ethyl; with the proviso that when $R_2$ is ethyl and $R_a$ is ethyl, then $R_2$ cannot be methyl. A particularly-preferred herbicide compound is the acetanilide compound of Formula IV:

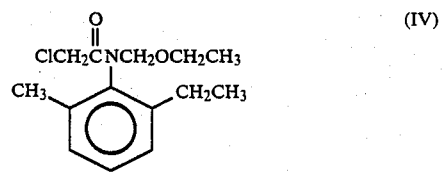

having the common name acetochlor and these alternative formal names:

2-chloro-N-(ethoxymethyl)-6'-ethyl-o-acetotoluidide or
2-chloro-2'-methyl-6'-ethyl-N-(ethoxymethyl)acetanilide or
2-chloro-N-ethoxymethyl-2'-methyl-6'-ethyl-acetanilide.

Another particularly-preferred acetanilide herbicide is the compound of Formula V:

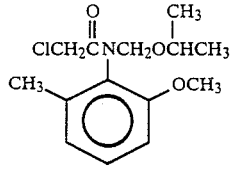

having the formal name 2-chloro-2'-methyl-6'-methoxy-N-(isopropoxymethyl)acetanilide. Another particularly preferred acetanilide herbicide is the compound of Formula VI:

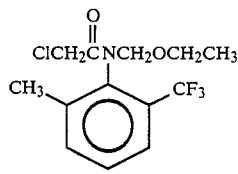

having the formal name 2-chloro-2'-methyl-6'-trifluoromethyl-N-(ethoxymethyl)acetanilide.

The terms "antidote", "safening agent", "safener", "antagonistic agent", "interferant", "crop protectant" and "crop protective", are often-used terms denoting a compound capable of reducing the phytotoxicity of a herbicide to a crop plant or crop seed. The terms "crop protectant" and "crop protective" are sometimes used to denote a herbicide-antidote combination which provides protection from competitive weed growth by reducing herbicidal injury to a valuable crop plant while at the same time controlling or suppressing weed growth occurring in the presence of the crop plant. Antidotes protect crop plants by interfering with the herbicidal action of a herbicide on the crop plants so as to render the herbicide selective to weed plants emerging or growing in the presence of crop plants.

Herbicides which may be used with benefit in combination with an antidote of the described class include thiocarbamates, triazines and acetamides. Such combinations can be used to obtain selective weed control with low crop injury in several varieties of monocotyledonous crop plants such as corn, grain sorghum (milo), and cereals such as wheat, rice, barley, oats and rye, as well as several varieties of dicotyledonous crop plants including oil-seed crops such as soybeans and cotton.

Examples of thiocarbamate herbicides are the following:
cis-/trans-2,3-dichloroallyl-diisopropylthiolcarbamate (common name "diallate");
ethyl dipropylthiocarbamate (common name "EPTC");
2,3,3-trichloroallyl-diisopropylthiolcarbamate (common name "triallate");
S-ethyl diisobutyl(thiocarbamate) (common name "butylate");
S-propyl dipropyl(thiocarbamate) (common name "vernolate").

Examples of triazine herbicides are the following:

2-chloro-4,6-bis(ethylamino)-1,3,5-triazine (common name "simazine");
2-chloro-4-ethylamino-6-isopropylamino-sym-triazine (common name "atrazine");
2-chloro-4-(1-cyano)-1-methyl(ethylamino)-6-ethylamino-1,3,5-triazine (common name "cyanazine");

Examples of acetamide herbicides are the following:
2-chloro-N-isopropylacetanilide (common name "propachlor");
2-chloro-2'-dimethylethyl)-6'-methyl-N-(methoxymethyl)acetanilide;
N-(butoxymethyl)-2-chloro-N-[2-(1,1-dimethylethyl)-6-methylphenyl]acetamide (common name "terbuchlor");
2-chloro-2',6'-diethyl-N-(methoxymethyl)acetanilide (common name "alachlor");
2-chloro-N-(isobutoxymethyl)-2',6'-acetoxylidide;
2-chloro-2',6'-diethyl-N-(butoxymethyl)acetanilide (common name "butachlor");
2-chloro-N-(ethoxymethyl)-6'-ethyl-o-acetotoluidide (common name "acetochlor");
2-chloro-N-(2,6-dimethyl-1-cyclohexen-1-yl)-N-(2-ethoxyethyl)acetamide;
ethyl ester of N-chloroacetyl-N-(2,6-diethylphenyl)glycine (common name "diethatyl ethyl");
2-chloro-N-(2,6-dimethylphenyl)-N-(2-methoxyethyl)acetamide (common name "dimethachlor");
2-chloro-N-(2-methoxy-1-methylethyl)-6'-ethyl-o-acetotoluidide (common name "metolachlor");
2-chloro-2',3'-dimethyl-N-(isopropyl)acetanilide;
2-chloro-2'-methyl-6'-methoxy-N-(propoxymethyl)acetanilide;
2-chloro-2'-methyl-6'-methoxy-N-(isopropoxymethyl)acetanilide;
2-chloro-2'-methyl-6'-ethoxy-N-(propoxymethyl)acetanilide;
N-(ethoxymethyl)-N-(2-ethyl-6-methyl-1-cyclohexen-1-yl)-2-chloroacetamide;
N-(ethoxymethyl)-N-(2,5-dimethyl-1-cyclopenten-1-yl)-2-chloroacetamide;
2-chloro-2',6'-dimethyl-N-(1-pyrazol-1-ylmethyl)acetanilide (common name "metazachlor");
2-chloro-N-(2,6-dimethyl-1-cyclohexen-1-yl)-N-(1H-pyrazol-1-ylmethyl)acetamide;
2-chloro-6'-trifluoromethyl-N-(isopropoxymethyl)acetanilide;
2-chloro-2'-methyl-6'-trifluoromethyl-N-(ethoxymethyl)acetanilide;
2-chloro-2'-trifluoromethyl-6-methyl-N-(propoxymethyl)acetanilide;
2-chloro-2'-methyl-6'-trifluoromethyl-N-(isopropoxymethyl)acetanilide;
2-chloro-2'-(3-methylbutoxy)-6'-methyl-N-(methyl)acetanilide;
2-chloro-2'-isobutoxy-6'-methyl-N-(propoxymethyl)acetanilide;
2-chloro-2'-methyl-6'-propoxy-N-(methyl)acetanilide;
2-chloro-2'-butoxy-6'-methyl-N-(methyl)acetanilide;
α-chloro-N-(ethoxymethyl)-N-[2-methyl-1-(1-methylethyl)-1-propenyl]acetamide;
2-chloro-2'-ethyl-6'-(2-methylpropoxy)-N-(ethoxymethyl)acetanilide;
2-chloro-2'-methyl-6'-(1-methylbutoxy)-N-(methyl)acetanilide;
2-chloro-2'-ethyl-6'-(1-methylpropyl)-N-(methyl)acetanilide;

2-chloro-2'-(1,3-dimethylbutoxy)-6'-methyl-N-(methyl-
)acetanilide;
2-chloro-2'-methyl-6'-(1-methylpropyl)-N-(methyl-
)acetanilide;
2-chloro-2'-ethyl-6'-trifluoromethyl-N-(1-pyrazolyl-1-
ylmethyl)acetanilide;
2-chloro-N-isopropyl-1-(3,5,5-trimethylcyclohexen-1-
yl)acetamide (common name "trimexachlor");

Several of the mentioned herbicides are known in the art. Diallate and triallate herbicides are described in U.S. Pat. Nos. 3,330,643 and 3,330,821. Atrazine herbicide is described in U.K. Pat. No. 814,947. Alachlor, butachlor and acetochlor herbicides are described in U.S. Pat. Nos. 3,442,945 or 3,547,620. Propachlor herbicide is described in U.S. Pat. No. 2,863,752 and U.S. Pat. No. Re. 26,961. Metolachlor herbicide is described in U.S. Pat. No. 3,937,730. Metazachlor herbicide is described in U.S. Pat. No. 4,249,935. Trimexachlor herbicide is described in U.S. Pat. No. 4,319,918. U.S. Pat. No. 4,351,667 describes the herbicides N-(ethoxymethyl)-N-(2-ethyl-6-methyl-1-cyclohexen-1-yl)-2-chloroacetamide and N-(ethoxymethyl)-N-2-(2,5-dimethyl-1-cyclopenten-2-yl)-2-chloroacetamide. U.K. Pat. No. 2,072,175 describes the herbicide 2-chloro-2'-methyl-6'-methoxy-N-(isopropoxymethyl)acetanilide. U.K. Pat. No. 2,072,181 describes the herbicide 2-chloro-2'-methyl-6'-trifluoromethyl-N-(ethoxymethyl-)acetanilide.

Combinations may be made of any one or more of the antidote compounds of Formula I with any one or more of the herbicide compounds mentioned herein.

ANTIDOTE COMPOUND PREPARATION

The 2-(dichloroacetyl)-3-substituted-1,2,3,4-tetrahydroisoquinoline antidote compounds of the following Examples 1-3 were prepared by the following general methods:

Step I:
A phenethyl halide is reacted with an alkyl nitrile in the presence of stannic chloride or sulfur chloride cyclizing agent to form a dihydroisoquinoline intermediate.

Step II:
The dihydroisoquinoline intermediate is reduced to a 3-substituted-1,2,3,4-tetrahydroisoquinoline. Reduction may occur by hydrogenation in the presence of a noble metal catalyst or by use of a borohydride compound.

Step III:
The resulting isoquinoline intermediate is then reacted with dichloroacetyl chloride to provide a 2-(dichloroacetyl)-3-substituted-1,2,3,4-tetrahydroisoquinoline.

The general description of Steps I-III does not cover the preparation of antidote compound of Example 4. This compound required a special method as shown in Example 4.

The following examples are presented for illustrative purposes and are not intended as a restriction on the scope of the invention. All parts are by weght unless otherwise indicated. Most of the commercially-available starting materials were obtained from Aldrich Chemical Co., Milwaukee, Wis.

EXAMPLE 1

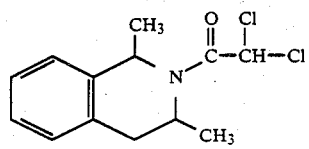

2-(Dichloroacetyl)-1,3-dimethyl-1,2,3,4-tetrahydroisoquinoline

A reaction vessel was charged with acetonitrile which was held under a nitrogen blanket. With the reaction vessel cooled in an ice bath, stannic chloride was added gradually below the surface of the acetonitrile with stirring over a period of 2 hours 20 minutes. During the addition period, the temperature of the reaction mixture varied between 3° C. and 39° C. The mixture was allowed to stand overnight at room temperature. With the reaction mixture at 22° C., α-methylphenethyl chloride was added in increments to the reaction vessel over a ten-minute period. With the mixture under reduced pressure and heated, acetonitrile nitrile was gradually stripped from the mixture. The reaction mixture, milky in color, was heated to reflux. The reaction mixture was maintained at reflux for about 6½ hours. With the temperature of the reaction mixture at about 75° C., the entire amount of previously-stripped acetonitrile was added back to the reaction mixture. The mixture was allowed to cool, stand overnight and was observed to contain a slurry. Methylene chloride was added to the mixture. Then, this mixture was added with stirring to 10% sodium hydroxide previously cooled to about 10° C. The temperature of the mixture reached 40° C. and the mixture was found to be acidic. More 10% sodium hydroxide was added to make the mixture alkaline. The organic phase was separated and washed with water. The organic phase was dried over sodium sulfate, filtered and stripped on a rotary evaporator at a temperature of 35°-40° C. to provide 1,3-dimethyl-3,4-dihyroisoquinoline. An autoclave was charged with a slurry of 50%-wetted 5% palladium-on-carbon catalyst in absolute ethanol. Then, there was added to the slurry a mixture of 1,3-dimethyl-3,4-dihydroisoquinoline. The autoclave was flushed with hydrogen gas. With the reaction mixture being stirred, the autoclave was gradually pressurized with hydrogen over a period of about two hours to a final pressure of about 185 psi (12.5 atm; $12.6 \times 10^5$ Pascal) and temperature of about 50° C. The autoclave was maintained in this pressurized condition overnight. The temperature of the autoclave dropped to about 10° C. after venting with stirring of the reaction mixture. The mixture was filtered and stripped of ethanol to provide 1,3-dimethyl-1,2,3,4-tetrahydroisoquinoline. A reaction vessel was charged with 2.5 g of 1,3-dimethyl-1,2,3,4-tetrahydroisoquinoline, 20 ml 10% sodium hydroxide and 50 ml methylene chloride. With this mixture stirred, 1.1 equivalents dichloro-acetyl chloride was added dropwise to the mixture. The mixture was stirred for 20 minutes, then water was added. The organic extract was dried with magnesium sulfate, and stripped of solvent, and then subjected to Kugelrohr distillation (150° C. @ 0.1 mm Hg) to provide 2.5 g of a yellow oil product having the following elemental analysis:

| $C_{13}H_{15}Cl_2NO$: | % Calc. | % Found |
|---|---|---|
| C | 57.37 | 57.75 |
| H | 5.56 | 5.98 |
| N | 5.15 | 4.85 |

EXAMPLE 2

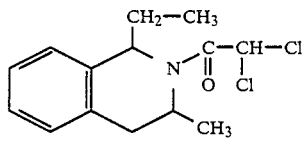

2-(Dichloroacetyl)-1-ethyl-3-methyl-1,2,3,4-tetrahydroisoquinoline

By procedures described in Example 1, α-methylphenethylchloride and propionitrile were converted to 1-ethyl-3-methyl-1,2,3,4-tetrahydroisoquinoline. A reaction vessel was charged with 4 g of this isoquinoline compound, 10 ml 10% sodium hydroxide and 50 ml methylene chloride. With this mixture stirred, 1.1 equivalents dichloro-acetyl chloride was added dropwise to the mixture. The mixture was stirred for 15 minutes, then water was added. The organic extract was dried with magnesium aulfate, and stripped of solvent, and subjected to Kugelrohr distillation (150° C. @0.25 mm Hg) to provide 4.5 g of a yellow oil product having the following elemental analysis:

| $C_{14}H_{17}Cl_2NO$: | % Calc. | % Found |
|---|---|---|
| C | 58.75 | 58.75 |
| H | 5.99 | 5.68 |
| N | 4.89 | 4.94 |

EXAMPLE 3

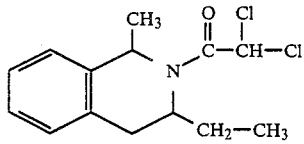

2-(Dichloroacetyl)-1-methyl-3-ethyl-1,2,3,4-tetrahydroisoquinoline

By procedures described in Example 1, α-ethylphenethyl chloride and acetonitrile were converted to 1-methyl-3-ethyl-1,2,3,4-tetrahydroisoquinoline. A reaction vessel was charged with 3 g of this isoquinoline compound, 10 ml 10% sodium hydroxide and 50 ml methylene chloride. With this mixture stirred, 1.1 equivalents dichloroacetyl chloride was added dropwise to the mixture. The mixture was stirred for 15 minutes, then water was added. The organic extract was dried with magnesium sulfate, stripped of solvent and chromatographed. A yellow oil product was recovered having the following elemental analysis:

| $C_{14}H_{17}Cl_2NO$: | % Calc. | % Found |
|---|---|---|
| C | 58.75 | 58.73 |
| H | 5.99 | 6.02 |

| $C_{14}H_{17}Cl_2NO$: | % Calc. | % Found |
|---|---|---|
| N | 4.89 | 5.01 |

EXAMPLE 4

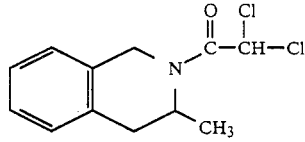

2-(DiChloroacetyl)-3-methyl-1,2,3,4-tetrahydroisoquinoline.

A reaction vessel was charged with 5 g of 3-methylisoquinoline, dry hydrogen chloride gas, ethanol toluene in order to form 3-methylisoquinoline. HCl salt. Solvent was removed from the mixture. The 3-methylisoquinoline salt was dissolved in methanol and platinum dioxide was added. This mixture was hydrogenated, in accordance generally with the procedure described in Example 1, which resulted in a mixture of 1,2,3,4-tetrahydroisoquinoline and 5,6,7,8-tetrahydroisoquinoline. This mixture was dissolved in 100 ml methylene chloride and then with stirring of this mixture, 2 ml of dichloroacetyl chloride was slowly added. The mixture was stirred for 15 minutes and then 50 ml of 35% HCl was added to remove 5,6,7,8-tetrahydroisoquinoline which did not react with dichloroacetyl chloride. The mixture was then stirred 10 minutes at room temperature. The mixture was then extracted with mwthylene chloride, dried with magnesium sulfate, and then solvent was removed. The residue was subjected to Kugelrohr distillation (130° C. @ 0.01 mm Hg) to give 1.8 g of a yellow oil product having the following elemental analysis:

| $C_{12}H_{13}Cl_2NO$: | % Calc. | % Found |
|---|---|---|
| C | 55.83 | 56.22 |
| H | 5.08 | 5.41 |
| N | 5.43 | 5.48 |

BIOLOGICAL EVALUATION

Effective weed control coupled with low crop injury is a result of treatment of a plant locus with a combination of herbicide compound and antidote compound. By application to the "plant locus" is meant application to the plant growing medium, such as soil, as well as to the seeds, emerging seedlings, roots, stems, leaves, or other plant parts.

The phrase "combination of herbicide compound and antidote compound" embraces various methods of treatment. For example, the soil of a plant locus may be treated with a "tank-mix" composition containing a mixture of the herbicide and the antidote which is "in combination". Or, the soil may be treated with the herbicide and antidote compounds separately so that the "combination" is made on, or in, the soil. After such treatments of the soil with a mixture of herbicide and antidote or by separate or sequential application of the herbicide and antidote to the soil, the herbicide and antidote may be mixed into or incorporated into the soil either by mechanical mixing of the soil with implements or by "watering in" by rainfall or irrigation. The soil of a plant locus may also be treated with antidote by application of the antidote in a dispersible-concentrate form such as a granule. The antidote-containing granule may be applied to a furrow which is prepared for receipt of the crop seed and the herbicide may be applied to the plant locus either before or after in-furrow placement of the antidote-containing granule so that the herbicide and antidote form a "combination". Crop seed may be treated or coated with the antidote compound either while the crop seed is in-furrow just after seeding or, more commonly, the crop seed may be treated or coated with antidote prior to seeding into a furrow. The herbicide may be applied to the soil plant locus before or after seeding and a "combination" is made when both herbicide and antidote-coated seed are in the soil. Also contemplated as a "combination" is a commercially-convenient association or presentation of separate components of herbicide and antidote. For example, the herbicide and antidote components in concentrated form may be contained in separate containers, with such containers presented for sale or sold together as a "combination". Or, the herbicide and antidote components in concentrated form may be in a mixture in a single container as a "combination". Either such "combination" may be diluted or mixed with adjuvants suitable for soil applications. Another example of a commercially-presented combination is a container of antidote-coated crop seed sold, or presented for sale, along with a container of herbicide material. These containers may, or may not, be physically attached to each other, but nonetheless constitute a "combination of herbicide and antidote" when intended for use ultimately in the same plant locus.

The amount of antidote employed in the methods and compositions of the invention will vary depending upon the particular herbicide with which the antidote is employed, the rate of application of the herbicide, the particular crop to be protected, and the manner of application to the plant locus. In each instance the amount of antidote employed is a safening-effective amount, that is, the amount which reduces, or protects against, crop injury that otherwise would result from the presence of the herbicide. The amount of antidote employed will be less than an amount that will substantially injure the crop plant.

The antidote can be applied to the crop plant locus in a mixture with the selected herbicide. For example, where the crop seed is first planted, a suitable mixture of antidote and herbicide, whether in a homogeneous liquid, emulsion, suspension or solid form, can be applied to the surface of, or incorporated in, the soil in which the seed has been planted. Or, the herbicide-antidote mixture may be applied to the soil, and then the seed thereafter "drilled" into the soil below the soil layer containing the herbicide-antidote mixture. The herbicide will reduce or eliminate the presence of undesirable weed plants. Where the herbicide would by itself injure the crop seedlings, the presence of the antidote will reduce or eliminate the injury to the crop seed caused by the herbicide. It is not essential that the application of herbicide and the antidote to the plant locus be made using the selected herbicide and antidote in the form of a mixture or composition. The herbicide and the antidote may be applied to the plant locus in a sequential manner. For example, the antidote may be first applied to the plant locus and thereafter the herbicide is applied. Or, the herbicide may be first applied to the plant locus and thereafter the antidote is applied.

The ratio of herbicide to antidote may vary depending upon the crop to be protected, weed to be inhibited, herbicide used, etc., but normally a herbicide-to-antidote ratio ranging from 1:25-to-50:1 (preferably 1:5-to-30:1) parts by weight may be employed. As indicated above, the antidote may be applied to the plant locus in a mixture, i.e., a mixture of a herbicidally-effective amount of herbicide and a safening-effective amount of an antidote, or sequentially, i.e., the plant locus may be treated with an effective amount of the herbicide followed by a treatment with the antidote or vice versa. In general, effective herbicidal amounts are in the range of about 0.2 to about 12 kilograms/hectare. The preferred range of rate of application is from about 0.4 to about 10 kg/h. Preferably, antidote application rates range from about 0.5 kg/ha down to about 0.05 kg/ha. It will be appreciated that at times amounts either below or above these ranges will be necessary to obtain the best results. The selection of the herbicide to inhibit the emergence and growth of weeds depends upon the species of weeds to be controlled and the crop to be protected.

The application of the antidote can be made directly to the seed before planting. In this practice, a quantity of crop seed is first coated with the antidote. The coated seed is thereafter planted. The herbicide may be applied to the soil before or after the coated seed is planted.

Evaluations of safening activity of the antidote compounds of this invention were carried out using the specific procedures of Examples 5-8 in greenhouse testing. Measurements of biological response as reported in Tables I-IV were made in the following manner. A visual comparison was made between a crop plant treated with herbicide alone and crop plant having no herbicide or antidote treatment ("untreated control"). A number was assigned to this visual comparison indicating the percent injury or inhibition to the herbicide-alone treated crop plant (column "WO" in Tables I-IV indicating herbicide "without" antidote). Also, a visual comparison was made between the crop plant treated with herbicide+antidote combination and the untreated control. A number was assigned to this visual comparison indicating the percent injury or inhibition to the herbicide+antidote treated crop plant (column "W" in Tables I-IV indicating herbicide "with" antidote). Where treatments involved weed plant species, observations of response to herbicide or herbicide+antidote were similarly recorded. The degree of reduction of herbicide injury provided by an antidote compound is indicated by the magnitude that the plant inhibition number of column "WO" exceeds the corresponding number of column "W". Also reported in Tables I-IV are data showing "safening effect" for the herbicide+antidote combinations calculated from the plant inhibition numbers. These tables show crop or weed column headings under which there are no data. The lack of such data is not an indication of a failed test; rather it is merely an indication that the particular herbicide/antidote rate combination was not tested with that crop or weed.

Summarized below is key information for interpreting data reported in Tables I-IV:

| Herbicide No. | Name |
|---|---|
| 1 | 2,3,3-trichloroallyldiisopropylthiocarbamate |

-continued

| Herbicide No. | Name |
|---|---|
| | (triallate) |
| 2 | 2-chloro-4-ethylamino-6-isopropylamino-1,3,5-triazine (atrazine) |
| 3 | 2-chloro-2',6'-diethyl-N—(methoxymethyl)-acetanilide (alachlor) |
| 4 | 2-chloro-2',6'-diethyl-N—(butoxymethyl)-acetanilide (butachlor) |
| 5 | 2-chloro-N—(ethoxymethyl)-6'-ethyl-o-aceto-toluidide (acetochlor) |
| 6 | 2-chloro-2'-methyl-6'-methoxy-N—(isopropoxymethyl)acetanilide |

Antidote No. = Compound in corresponding Example No.
Rate = Kilograms/hectare (kg/ha).
W = % Plant Inhibition caused by combination of herbicide and antidote.

furrows of the third container. Antidote application rate was 0.55 mg active compound per inch of furrow. This rate was comparable to a plot application rate of 0.28 kilogram per hectare (Kg/ha), based on 76 cm (30″) spaced-apart furrows. Then, each of the second and third containers was filled and leveled with a cover layer of soil having incorporated therein the selected herbicide at a pre-determined concentration. The first container was filled and leveled with soil containing no herbicide. The containers were then placed on a greenhouse bench and sub-irrigated as required for the duration of the test. Plant response was observd about three weeks after initial treatment. Results are reported in Table I.

TABLE I

| | | | | % PLANT INHIBITION AND % SAFENING EFFECT ( ) | | | | | | | | | |
|---|---|---|---|---|---|---|---|---|---|---|---|---|---|
| HERBICIDE | | ANTIDOTE | | GRAIN SORGHUM | | WHEAT | | RICE | | SOYBEAN | | CORN | |
| NO. | RATE | NO. | RATE | W | WO | W | WO | W | WO | W | WO | W | WO |
| 1 | 0.56 | 1 | 0.28 | | | 70 (26) | 95 | | | | | | |
| 1 | 0.56 | 2 | 0.28 | | | 85 (10) | 95 | | | | | | |
| 1 | 0.56 | 4 | 0.28 | | | 85 (15) | 100 | | | | | | |
| 2 | 4.48 | 1 | 0.28 | | | | | | | 75 (0) | 55 | | |
| 2 | 4.48 | 2 | 0.28 | | | | | | | 40 (50) | 80 | | |
| 3 | 2.24 | 1 | 0.28 | 100 (0) | 100 | 90 (10) | 100 | | | | | | |
| 3 | 2.24 | 2 | 0.28 | 95 (5) | 100 | 60 (36) | 95 | | | | | | |
| 3 | 2.24 | 4 | 0.28 | 10 (89) | 95 | 90 (10) | 100 | | | | | | |
| 4 | 4.48 | 1 | 0.28 | | | | | 100 (0) | 100 | | | | |
| 4 | 4.48 | 2 | 0.28 | | | | | 85 (10) | 95 | | | | |
| 4 | 4.48 | 4 | 0.28 | | | | | 80 (11) | 90 | | | | |
| 6 | 2.24 | 1 | 0.28 | | | | | | | 85 (0) | 75 | 40 (57) | 95 |
| 6 | 2.24 | 2 | 0.28 | | | | | | | 60 (25) | 80 | 30 (68) | 95 |
| 6 | 2.24 | 4 | 0.28 | | | | | | | 30 (53) | 65 | 30 (68) | 95 |
| 1 | 0.56 | 3 | 0.28 | | | 85 (5) | 90 | | | | | | |
| 3 | 2.24 | 3 | 0.28 | 40 (57) | 95 | 80 (11) | 90 | | | | | | |
| 4 | 4.48 | 3 | 0.28 | | | | | 95 (0) | 95 | | | | |
| 6 | 2.24 | 3 | 0.28 | | | | | | | 30 (57) | 70 | 85 (15) | 100 |

WO = % Plant Inhibition caused by herbicide alone.
Data reported in parentheses = % Safening Effect
$( \_ ) = \frac{WO - W}{WO} \times 100$

EXAMPLE 5

The following procedure shows interaction between a herbicide and antidote when the antidote is applied to a soil furrow containing crop seed and the herbicide is incorporated in a soil cover layer. Containers were filled and compacted with fumigated silt loam soil to a depth of about 1.3 cm from the top of the container. A first container was designated as an untreated control, a second container was designated as a herbicide control, and a third container was designated as a herbicide+antidote test container. Each container was seeded with crop seed in marked furrows. Antidote compound, dissolved in acetone, was applied directly to the seeded

EXAMPLE 6

The following procedure shows interaction between herbicide and antidote when both are incorporated in a soil cover layer before emergence of the crop. Containers were filled and compacted with a fumigated silt loam top soil to a depth of about 1.3 cm from the top of the container. A first container was designated as an untreated control, a second container was designated as a herbicide control, and a third container was designated as a herbicide+antidote test container. Each of the containers was seeded with a crop species. A measured amount of herbicide dispersed or dissolved in acetone was applied to a measured quantity of soil. To this same quantity of soil treated with herbicide, there was added a measured amount of antidote dispersed or dissolved in acetone. The quantity of soil treated with the herbicide and antidote was thoroughly mixed to incorporate the herbicide and antidote in the soil uniformly. The seed bed in the third container was covered with the soil treated with the herbicide and antidote and the container was leveled. For each test series, the seed beds of the first and second containers were likewise covered by soil layers. The cover layer of the first container was not treated with herbicide or antidote. The cover layer of the second container had a measured quantity of herbicide alone incorporated therein. The containers were then placed on a bench in a greenhouse and sub-irrigated as required for the duration of the test. Plant response was observed about three weeks after initial treatment. Results are reported in Table II.

TABLE II

| HERBICIDE | | ANTIDOTE | | % PLANT INHIBITION AND % SAFENING EFFECT ( ) | | | | | | | |
|---|---|---|---|---|---|---|---|---|---|---|---|
| NO. | RATE | NO. | RATE | GRAIN SORGHUM | | CORN | | BARNYARD GRASS | | GREEN FOXTAIL | |
| | | | | W | WO | W | WO | W | WO | W | WO |
| 3 | 0.56 | 4 | 0.56 | 45 (52) | 95 | | | | | 95 (5) | 100 |
| 3 | 0.56 | 4 | 2.24 | 40 (57) | 95 | | | | | 100 (0) | 100 |
| 3 | 0.56 | 4 | 8.96 | 25 (73) | 95 | | | | | 95 (5) | 100 |
| 3 | 2.24 | 4 | 0.56 | 95 (0) | 95 | | | | | 100 (0) | 100 |
| 3 | 2.24 | 4 | 2.24 | 70 (26) | 95 | | | | | 100 (0) | 100 |
| 3 | 2.24 | 4 | 8.96 | 75 (21) | 95 | | | | | 100 (0) | 100 |
| 6 | 0.56 | 1 | 0.56 | | | 0 (100) | 30 | 95 (0) | 95 | | |
| 6 | 0.56 | 1 | 2.24 | | | 0 (100) | 30 | 95 (0) | 95 | | |
| 6 | 0.56 | 1 | 8.96 | | | 0 (100) | 30 | 95 (0) | 95 | | |
| 6 | 2.24 | 1 | 0.56 | | | 20 (60) | 50 | 100 (0) | 95 | | |
| 6 | 2.24 | 1 | 2.24 | | | 10 (80) | 50 | 100 (0) | 95 | | |
| 6 | 2.24 | 1 | 8.96 | | | 5 (90) | 50 | 100 (0) | 95 | | |
| 6 | 0.56 | 2 | 0.56 | | | 0 (100) | 35 | 95 (0) | 95 | | |
| 6 | 0.56 | 2 | 2.24 | | | 5 (85) | 35 | 90 (5) | 95 | | |
| 6 | 0.56 | 2 | 8.96 | | | 5 (85) | 35 | 85 (10) | 95 | | |
| 6 | 2.24 | 2 | 0.56 | | | 15 (76) | 65 | 100 (0) | 100 | | |
| 6 | 2.24 | 2 | 2.24 | | | 10 (84) | 65 | 95 (5) | 100 | | |
| 6 | 2.24 | 2 | 8.96 | | | 5 (92) | 65 | 100 (0) | 100 | | |
| 6 | 0.56 | 4 | 0.56 | | | 40 (52) | 85 | 100 (0) | 100 | | |
| 6 | 0.56 | 4 | 0.56 | | | 10 (60) | 25 | 95 (0) | 95 | | |
| 6 | 0.56 | 4 | 2.24 | | | 95 (0) | 85 | 100 (0) | 100 | | |
| 6 | 0.56 | 4 | 2.24 | | | 0 (100) | 25 | 100 (0) | 95 | | |
| 6 | 0.56 | 4 | 8.96 | | | 0 (100) | 85 | 100 (0) | 100 | | |
| 6 | 0.56 | 4 | 8.96 | | | 0 (100) | 25 | 95 (0) | 95 | | |
| 6 | 2.24 | 4 | 0.56 | | | 15 (83) | 90 | 100 (0) | 100 | | |
| 6 | 2.24 | 4 | 0.56 | | | 70 (26) | 95 | 100 (0) | 100 | | |
| 6 | 2.24 | 4 | 2.24 | | | 5 (94) | 90 | 100 (0) | 100 | | |
| 6 | 2.24 | 4 | 2.24 | | | 95 (0) | 95 | 100 (0) | 100 | | |
| 6 | 2.24 | 4 | 8.96 | | | 0 (100) | 90 | 100 (0) | 100 | | |
| 6 | 2.24 | 4 | 8.96 | | | 5 (94) | 95 | 100 (0) | 100 | | |

| HERBICIDE | | ANTIDOTE | | GRAIN SORGHUM | | GREEN FOXTAIL | | CORN | | BARNYARD GRASS | | SOYBEAN | |
|---|---|---|---|---|---|---|---|---|---|---|---|---|---|
| NO. | RATE | NO. | RATE | W | WO | W | WO | W | WO | W | WO | W | WO |
| 3 | 0.56 | 3 | 0.56 | 75 (0) | 70 | 100 (0) | 100 | | | | | | |

TABLE II-continued

| | | | | % PLANT INHIBITION AND % SAFENING EFFECT ( ) | | | | | | | | | | |
|---|---|---|---|---|---|---|---|---|---|---|---|---|---|---|
| HERBICIDE | | ANTIDOTE | | | | | | | | | | | | |
| NO. | RATE | NO. | RATE | | | | | | | | | | | |
| 3 | 0.56 | 3 | 2.24 | 55 (21) | 70 | 95 (5) | 100 | | | | | | | |
| 3 | 0.56 | 3 | 8.96 | 65 (7) | 70 | 100 (0) | 100 | | | | | | | |
| 3 | 2.24 | 3 | 0.56 | 95 (0) | 95 | 100 (0) | 100 | | | | | | | |
| 3 | 2.24 | 3 | 2.24 | 75 (21) | 95 | 100 (0) | 100 | | | | | | | |
| 3 | 2.24 | 3 | 8.96 | 80 (15) | 95 | 100 (0) | 100 | | | | | | | |
| 6 | 0.56 | 3 | 0.56 | | | | | 45 (43) | 80 | 100 (0) | 100 | | | |
| 6 | 0.56 | 3 | 2.24 | | | | | 55 (31) | 80 | 100 (0) | 100 | | | |
| 6 | 0.56 | 3 | 8.96 | | | | | 15 (81) | 80 | 100 (0) | 100 | | | |
| 6 | 1.12 | 3 | 0.56 | | | | | | | 100 (0) | 95 | 20 (0) | 15 | |
| 6 | 1.12 | 3 | 2.24 | | | | | | | 100 (0) | 95 | 25 (0) | 15 | |
| 6 | 1.12 | 3 | 8.96 | | | | | | | 100 (0) | 95 | 40 (0) | 15 | |
| 6 | 2.24 | 3 | 0.56 | | | | | 85 (10) | 95 | 100 (0) | 100 | | | |
| 6 | 2.24 | 3 | 2.24 | | | | | 55 (42) | 95 | 100 (0) | 100 | | | |
| 6 | 2.24 | 3 | 8.96 | | | | | 20 (78) | 95 | 100 (0) | 100 | | | |
| 6 | 4.48 | 3 | 0.56 | | | | | | | 100 (0) | 100 | 65 (0) | 50 | |
| 6 | 4.48 | 3 | 2.24 | | | | | | | 100 (0) | 100 | 65 (0) | 50 | |
| 6 | 4.48 | 3 | 8.96 | | | | | | | 100 (0) | 100 | 50 (0) | 50 | |

EXAMPLE 7

The following procedure shows interaction between a herbicide and antidote when applied together as a mixture before emergence of the crop and weed species. Containers were filled and compacted with fumigated silt loam top soil to a depth of about 1.3 cm from the top of the container. A first container was designated as an untreated control, a second container was designated as a herbicide control, and a third container was designated as a herbicide+antidote test container. Each of the containers was seeded with both crop plant and weed species. The herbicide alone and the herbicide+antidote mixture were applied to the seeded containers either by a procedure of topical application to a soil layer placed over the seed bed followed by watering to achieve incorporation, or by a procedure of incorporation into soil and then placement of the treated soil into the container over the seed bed. The containers were then placed on a greenhouse bench and sub-irrigated as required for the duration of the test. Plant response was observed about three weeks after initial treatment. Results are reported in Table III

TABLE III

| | | | | % PLANT INHIBITION AND % SAFENING EFFECT ( ) | | | | | | | |
|---|---|---|---|---|---|---|---|---|---|---|---|
| HERBICIDE | | ANTIDOTE | | CORN | | GREEN FOXTAIL | | BARNYARD GRASS | | CRAB GRASS | |
| NO. | RATE | NO. | RATE | W | WO | W | WO | W | WO | W | WO |
| 5 | 4.48 | 2 | 0.14 | 0 (100) | 20 | 100 (0) | 100 | 100 (0) | 99 | | |
| 5 | 4.48 | 2 | 0.56 | 5 (75) | 20 | 100 (0) | 100 | 100 (0) | 98 | | |
| 5 | 4.48 | 2 | 2.24 | 0 (100) | 20 | 100 (0) | 100 | 100 (0) | 98 | | |
| 5 | 6.72 | 2 | 0.14 | 0 (100) | 55 | 100 (0) | 100 | 100 (0) | 100 | | |
| 5 | 6.72 | 2 | 0.56 | 8 (85) | 55 | 100 (0) | 100 | 100 (0) | 100 | | |
| 5 | 6.72 | 2 | 2.24 | 5 (90) | 55 | 100 (0) | 100 | 100 (0) | 100 | | |
| 5 | 8.96 | 2 | 0.14 | 5 (88) | 45 | 100 (0) | 100 | 100 (0) | 100 | | |
| 5 | 8.96 | 2 | 0.56 | 15 (66) | 45 | 100 (0) | 100 | 100 (0) | 100 | | |
| 5 | 8.96 | 2 | 2.24 | 0 (100) | 45 | 100 (0) | 100 | 100 (0) | 100 | | |
| 6 | 1.12 | 1 | 0.14 | 8 (82) | 47 | 98 (0) | 95 | 98 (0) | 95 | | |
| 6 | 1.12 | 1 | 0.56 | 0 | 47 | 95 | 95 | 98 | 95 | | |

TABLE III-continued

% PLANT INHIBITION AND % SAFENING EFFECT ( )

| HERBICIDE | | ANTIDOTE | | CORN | | GREEN FOXTAIL | | BARNYARD GRASS | | CRAB GRASS | |
|---|---|---|---|---|---|---|---|---|---|---|---|
| NO. | RATE | NO. | RATE | W | WO | W | WO | W | WO | W | WO |
| 6 | 1.12 | 1 | 2.24 | 23 (51) | 47 | 95 (0) | 95 | 95 (0) | 95 | | |
| 6 | 2.24 | 1 | 0.14 | 10 (87) | 78 | 95 (3) | 98 | 100 (0) | 100 | | |
| 6 | 2.24 | 1 | 0.56 | 10 (87) | 78 | 95 (3) | 98 | 100 (0) | 100 | | |
| 6 | 2.24 | 1 | 2.24 | 5 (93) | 78 | 95 (3) | 98 | 95 (5) | 100 | | |
| 6 | 4.48 | 1 | 0.14 | 63 (27) | 87 | 100 (0) | 100 | 98 (2) | 100 | | |
| 6 | 4.48 | 1 | 0.56 | 60 (31) | 87 | 95 (5) | 100 | 100 (0) | 100 | | |
| 6 | 4.48 | 1 | 2.24 | 33 (62) | 87 | 100 (0) | 100 | 100 (0) | 100 | | |
| 6 | 1.12 | 2 | 0.14 | 25 (73) | 93 | 100 (0) | 100 | 98 (2) | 100 | | |
| 6 | 1.12 | 2 | 0.56 | 0 (100) | 93 | 100 (0) | 100 | 100 (0) | 100 | | |
| 6 | 1.12 | 2 | 2.24 | 5 (94) | 93 | 100 (0) | 100 | 95 (5) | 100 | | |
| 6 | 2.24 | 2 | 0.14 | 53 (35) | 82 | 98 (2) | 100 | 100 (0) | 100 | | |
| 6 | 2.24 | 2 | 0.56 | 28 (65) | 82 | 100 (0) | 100 | 100 (0) | 100 | | |
| 6 | 2.24 | 2 | 2.24 | 0 (100) | 82 | 100 (0) | 100 | 100 (0) | 100 | | |
| 6 | 4.48 | 2 | 0.14 | 88 (0) | 73 | 100 (0) | 100 | 100 (0) | 100 | | |
| 6 | 4.48 | 2 | 0.56 | 60 (17) | 73 | 100 (0) | 100 | 100 (0) | 100 | | |
| 6 | 4.48 | 2 | 2.24 | 20 (72) | 73 | 100 (0) | 100 | 100 (0) | 100 | | |
| 6 | 1.12 | 4 | 0.14 | 20 (77) | 90 | 100 (0) | 100 | 100 (0) | 100 | | |
| 6 | 1.12 | 4 | 0.56 | 8 (91) | 90 | 100 (0) | 100 | 100 (0) | 100 | | |
| 6 | 1.12 | 4 | 2.24 | 5 (94) | 90 | 100 (0) | 100 | 100 (0) | 100 | | |
| 6 | 2.24 | 4 | 0.14 | 93 (0) | 85 | 100 (0) | 100 | 100 (0) | 100 | | |
| 6 | 2.24 | 4 | 0.56 | 63 (25) | 85 | 100 (0) | 100 | 100 (0) | 100 | | |
| 6 | 2.24 | 4 | 2.24 | 5 (94) | 85 | 100 (0) | 100 | 100 (0) | 100 | | |
| 6 | 4.48 | 4 | 0.14 | 95 (3) | 98 | 100 (0) | 100 | 100 (0) | 100 | | |
| 6 | 4.48 | 4 | 0.56 | 95 (3) | 98 | 100 (0) | 100 | 100 (0) | 100 | | |
| 6 | 4.48 | 4 | 2.24 | 40 (59) | 98 | 100 (0) | 100 | 100 (0) | 100 | | |
| 6 | 1.12 | 3 | 0.14 | 80 (11) | 90 | 100 (0) | 100 | 100 (0) | 100 | | |
| 6 | 1.12 | 3 | 0.56 | 20 (77) | 90 | 100 (0) | 100 | 100 (0) | 100 | | |
| 6 | 1.12 | 3 | 2.24 | 0 (100) | 90 | 100 (0) | 100 | 100 (0) | 100 | | |
| 6 | 2.24 | 3 | 0.14 | 90 (0) | 85 | 100 (0) | 100 | 100 (0) | 100 | | |
| 6 | 2.24 | 3 | 0.56 | 55 (88) | 85 | 100 (0) | 100 | 100 (0) | 100 | | |
| 6 | 2.24 | 3 | 2.24 | 10 (88) | 85 | 100 (0) | 100 | 100 (0) | 100 | | |
| 6 | 4.48 | 3 | 0.14 | 95 (3) | 98 | 100 (0) | 100 | 100 (0) | 100 | | |
| 6 | 4.48 | 3 | 0.56 | 93 (5) | 98 | 100 (0) | 100 | 100 (0) | 100 | | |
| 6 | 4.48 | 3 | 2.24 | 33 (66) | 98 | 100 (0) | 100 | 100 (0) | 100 | | |

EXAMPLE 8

The procedure of Example 5 was followed to determine the interaction between herbicide and antidote when the antidote is applied to a soil furrow containing crop seed and the herbicide is incorporated in a soil cover layer. In this series of tests, however, all containers were seeded with at least one weed species in addition to crop seed. Plant response was observed about three weeks after initial treatment. Results are reported in Table IV.

TABLE IV

| | | | | % PLANT INHIBITION AND % SAFENING EFFECT ( ) | | | | | | |
|---|---|---|---|---|---|---|---|---|---|---|
| HERBICIDE | | ANTIDOTE | | CORN | | GREEN FOXTAIL | | BARNYARD GRASS | | CRAB GRASS |
| NO. | RATE | NO. | RATE | W | WO | W | WO | W | WO | W WO |
| 6 | 1.12 | 4 | 0.14 | 18 (45) | 33 | 100 (0) | 100 | 100 (0) | 95 | |
| 6 | 1.12 | 4 | 0.56 | 0 (100) | 33 | 98 (2) | 100 | 98 (0) | 95 | |
| 6 | 1.12 | 4 | 2.24 | 13 (60) | 33 | 100 (0) | 100 | 95 (0) | 95 | |
| 6 | 2.24 | 4 | 0.14 | 73 (0) | 73 | 100 (0) | 100 | 100 (0) | 100 | |
| 6 | 2.24 | 4 | 0.56 | 0 (100) | 73 | 100 (0) | 100 | 100 (0) | 100 | |
| 6 | 2.24 | 4 | 2.24 | 5 (93) | 73 | 100 (0) | 100 | 98 (2) | 100 | |
| 6 | 4.48 | 4 | 0.14 | 90 (0) | 82 | 100 (0) | 100 | 100 (0) | 100 | |
| 6 | 4.48 | 4 | 0.56 | 58 (29) | 82 | 100 (0) | 100 | 100 (0) | 100 | |
| 6 | 4.48 | 4 | 2.24 | 23 (71) | 82 | 100 (0) | 100 | 100 (0) | 100 | |

The foregoing examples illustrate that the combinations of herbicide and antidote of this invention are useful in controlling weeds while reducing herbicidal injury to crop plants under greenhouse test conditions.

In field applications, the herbicide, antidote, or a mixture thereof, may be applied to the plant locus without any adjuvants other than a solvent. Usually, the herbicide, antidote, or a mixture thereof, is applied in conjunction with one or more adjuvants in liquid or solid form. Compositions or formulations containing mixtures of an appropriate herbicide and antidote usually are prepared by admixing the herbicide and antidote with one or more adjuvants such as diluents, solvents, extenders, carriers, conditioning agents, water, wetting agents, dispersing agents, or emulsifying agents, or any suitable combination of these adjuvants. These mixtures may be in the form of particulate solids, granules, pellets, wettable powders, dusts, solutions, aqueous dispersions, or emulsions.

Examples of suitable adjuvants are finely-divided solid carriers and extenders including talcs, clays, pumice, silica, diatomaceous earth, quartz, Fuller's earth, sulfur, powdered cork, powdered wood, walnut flour, chalk, tobacco dust, charcoal, and the like. Typical liquid diluents include Stoddard's solvent, acetone, methylene chloride, alcohols, glycols, ethyl acetate, benzene, and the like. Liquids and wettable powders usually contain as a conditioning agent one or more surface-active agents in amounts sufficient to make a composition readily dispersible in water or in oil. The term "surface-active agent" includes wetting agents, dispersing agents, suspending agents, and emulsifying agents. Typical surface-active agents are mentioned in U.S. Pat. No. 2,547,724.

Compositions of this invention generally contain from about 5 to 95 parts herbicide-and-antidote, about 1 to 50 parts surface-active agent, and about 4 to 94 parts solvent, all parts being by weight based on the total weight of the composition.

Application of the herbicide, antidote, or mixture thereof, can be carried out by conventional techniques utilizing, for example, hand-carried or tractor-mounted spreaders, power dusters, boom and hand sprayers, spray dusters, and granular applicators. If desired, application of the compositions of the invention to plants can be accomplished by incorporating the compositions in the soil or other media.

The crop may be protected by treating the crop seed with an effective amount of antidote prior to planting. Generally, smaller amounts of antidote are required to treat such seeds. A weight ratio of as little as 0.6 parts of antidote per 1000 parts of seed may be effective. The amount of antidote utilized in treating the seed may be increased if desired. Generally, however, a weight ratio of antidote-to-seed weight may range from 0.1 to 10.0 parts of antidote per 1000 parts of seed. Since only a very small amount of active antidote is usually required for the seed treatment, the compound preferably is formulated as an organic solution, powder, emulsifiable concentrate, water solution, or flowable formulation, which can be diluted with water by the seed treater for use in seed treating apparatus. Under certain conditions, it may be desirable to dissolve the antidote in an organic solvent or carrier for use as a seed treatment or the pure compound alone may be used under properly controlled conditions.

For antidote seed-coating or for antidotes applied to soil in granular or liquid formulations, suitable carriers may be either solids, such as talc, sand, clay, diatomaceous earth, sawdust, calcium carbonate, and the like, or liquids, such as water, kerosene, acetone, benzene, toluene, xylene, and the like, in which the active antidote may be either dissolved or dispersed. Emulsifying agents are used to achieve a suitable emulsion if two immiscible liquids are used as a carrier. Wetting agents may also be used to aid in dispersing the active antidote in liquids used as a carrier in which the antidote is not completely soluble. Emulsifying agents and wetting agents are sold under numerous tradenames and trademarks and may be either pure compounds, mixtures of compounds of the same general groups, or they may be mixtures of compounds of different classes. Typical satisfactory surface active agents which may be used are alkali metal higher-alkylarylsulfonates such as sodium dodecylbenzenesulfonate, and the sodium salts of alkylnaphthalenesulfonic acids, fatty alcohol sulfates such as the sodium salts of monoesters of sulfuric acid with n-aliphatic alcohols containing 8–18 carbon atoms, long-chain quaternary ammonium sodium salts of petroleum-derived alkylsulfonic acids, polyethylene sorbitan monooleate, alkylaryl polyether alcohols, water-soluble lignin sulfonate salts, alkali casein compositions, long-chain alcohols usually containing 1–18 carbon atoms, and condensation products of ethylene oxide with fatty acids, alkylphenols, and mercaptans.

Although this invention has been described with respect to specific embodiments, the details of these embodiments are not to be construed as limitations. Various equivalents, changes, and modifications may be made without departing from the spirit and scope of this invention, and it is understood that such equivalent embodiments are part of this invention.

What is claimed is:

1. A method for reducing herbicide injury to a crop plant due to the application of a herbicidally-effective amount of a herbicide compound selected from thiocarbamates, triazines and acetamides and to the crop plant locus, which method comprises applying to the crop plant locus a safening-effective amount of at least one antidote compound of the formula

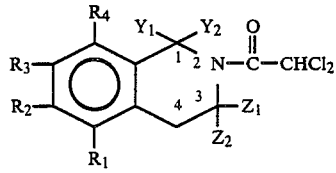

wherein each of $Y_1$, $Y_2$, $Z_1$ and $Z_2$ is independently selected from hydrido, alkyl and haloalkyl, with the proviso that at least one of $Z_1$ and $Z_2$ must be a group other than hydrido; and wherein each of $R_1$, $R_2$, $R_3$ and $R_4$ is independently selected from hydrido, alkyl, alkoxy and haloalkyl.

2. The method of claim 1 wherein each of $Y_1$, $Y_2$, $Z_1$ and $Z_2$ is independently selected from hydrido, linear or branched alkyl of one to ten carbon atoms and perfluoroalkyl; and wherein each of $R_1$, $R_2$, $R_3$ and $R_4$ is independently selected from hydrido and linear or branched alkyl of one to ten carbon atoms.

3. The method of claim 2 wherein each of $Y_1$, $Y_2$, $Z_1$ and $Z_2$ is independently selected from hydrido, linear or branched alkyl of one to five carbon atoms and trifluoromethyl; and wherein each of $R_1$, $R_2$, $R_3$ and $R_4$ is hydrido.

4. The method of claim 3 wherein said herbicide compound is an acetamide or thiocarbamate and said crop plant is corn.

5. The method of claim 4 wherein said antidote compound is 2-(dichloroacetyl)-1,3-dimethyl-1,2,3,4-tetrahydroisoquinoline.

6. The method of claim 4 wherein said antidote compound is 2-(dichloroacetyl)-1-ethyl-3-methyl-1,2,3,4-tetrahydroisoquinoline.

7. The method of claim 4 wherein said antidote compound is 2-(dichloroacetyl)-1-methyl-3-ethyl-1,2,3,4-tetrahydroisoquinoline.

8. The method of claim 4 wherein said antidote compound is 2-(dichloroacetyl)-3-methyl-1,2,3,4-tetrahydroisoquinoline.

9. The method of claim 4 wherein said herbicide compound is an acetamide herbicide compound.

10. The method of claim 9 wherein said acetamide herbicide compound is 2-chloro-2',6'-diethyl-N-(methoxymethyl)acetanilide.

11. The method of claim 9 wherein said aceamide herbicide compound is 2-chloro-N-(ethoxymethyl)-6'-ethyl-o-acetotoluidide.

12. The method of claim 9 wherein said acetamide herbicide compound is 2-chloro-N-(2-methoxy-1-methylethyl)-6'-ethyl-o-acetotoluidide.

13. The method of claim 9 wherein said acetamide herbicide compound is 2-chloro-2'-methyl-6'-methoxy-N-(isopropoxymethyl)acetanilide.

14. The method the of claim 9 wherein said acetamide herbicide compound is 2-chloro-2',6'-dimethyl-N-(1-pyrazol-1-ylmethyl)acetanilide.

15. The method of claim 9 wherein said acetamide herbicide compound is 2-chloro-2'-methyl-6'-trifluoromethyl-N-(ethoxymethyl)acetanilide.

16. The method of claim 9 wherein said acetamide herbicide compound is 2-chloro-N-isopropyl-1-(3,5,5-trimethylcyclohexen-1-yl)acetamide.

17. A combination comprising a herbicidally effective amount of a herbicide compound selected from thiocarbamates, triazines and acetamides, and a safening effective amount of an antidote compound of the formula

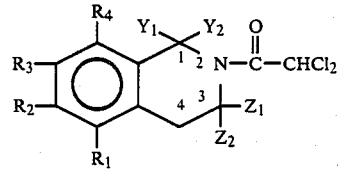

wherein each of $Y_1$, $Y_2$, $Z_1$ and $Z_2$ is independently selected from hydrido, alkyl and haloalkyl, with the proviso that at least one of $Z_1$ and $Z_2$ must be a group other than hydrido; and wherein each of $R_1$, $R_2$, $R_3$ and $R_4$ is independently selected from hydrido, alkyl, alkoxy and haloalkyl.

18. The combination of claim 17 wherein each of $Y_1$, $Y_2$, $Z_1$ and $Z_2$ is independently selected from hydrido, linear or branched alkyl of one to ten carbon atoms and perfluoroalkyl; and wherein each of $R_1$, $R_2$, $R_3$ and $R_4$ is independently selected from hydrido and linear or branched alkyl of one to ten carbon atoms.

19. The combination of claim 18 wherein each of $Y_1$, $Y_2$, $Z_1$ and $Z_2$ is independently selected from hydrido, linear or branched alkyl of one to five carbon atoms, and trifluoromethyl; and wherein each of $R_1$, $R_2$, $R_3$ and $R_4$ is hydrido.

20. The combination of claim 17 wherein said herbicide compound is an acetamide herbicide compound.

21. The combination of claim 20 wherein said acetamide herbicide compound is 2-chloro-2',6'-diethyl-N-(methoxymethyl)acetanilide.

22. The combination of claim 20 wherein said acetamide herbicide compound is 2-chloro-N-(ethoxymethyl)-6'-ethyl-o-acetotoludide.

23. The combination of claim 20 wherein said acetamide herbicide compound is 2-chloro-N-(2,6-dimethylphenyl)-N-(2-methoxyethyl)acetamide.

24. The combination of claim 20 wherein said acetamide herbicide compound is 2-chloro-N-(2-methoxy-1-methylethyl)-6'-ethyl-o-acetotoluidide.

25. The combination of claim 20 wherein said acetamide herbicide compound is 2-chloro-2'-methyl-6'-methoxy-N-(isopropoxymethyl)acetanilide.

26. The combination of claim 20 wherein said acetamide herbicide compound is 2-chloro-2',6'-dimethyl-N-(1-pyrazol-1-ylmethyl)acetanilide.

27. The combination of claim 20 wherein said acetamide herbicide compound is 2-chloro-2'-methyl-6'-trifluoromethyl-N-(ethoxymethyl)acetanilide.

28. The combination of claim 20 wherein said acetamide herbicide compound is 2-chloro-N-isopropyl-1-(3,5,5-trimethylcyclohexen-1-yl)acetamide.

29. The combination of claim 19 wherein said antidote compound is 2-(dichloroacetyl)-1,3-dimethyl 1,2,3,4-tetrahydroisoquinoline.

30. The combination of claim 19 wherein said antidote compound is 2-(2-chloroacetyl)-1-ethyl-3-methyl-1,2,3,4-tetrahydroisquinoline.

31. The combination of claim 19 wherein said antidote compound is 2-(dichloroacetyl)-1-methyl-3-ethyl-1,2,3,4-tetrahydroisoquinoline.

32. The combination of claim 19 wherein said antidote compound is 2-(dichloroacetyl)-3-methyl-1,2,3,4-tetrahydroisoquinoline.

33. A combination comprising: 2-(dichloroacetyl)-1,3-dimethyl-1,2,3,4-tetrahydroisoquinoline and 2-chloro-2',6'-diethyl-N-(methoxymethyl)acetanilide.

34. A combination comprising: 2-(dichloroacetyl)-1,3-dimethyl-1,2,3,4-tetrahydroisoquinoline and 2-chloro-N-(ethoxymethyl)-6'-ethyl-o-acetotoluidide.

35. A combination comprising: 2-(dichloroacetyl)-1,3-dimethyl-1,2,3,4-tetrahydroisoquinoline and 2-chloro-N-(2-methoxy-1-methylethyl)-6'-ethyl-o-acetotoluidide.

36. A combination comprising: 2-(dichloroacetyl)-1,3-dimethyl-1,2,3,4-tetrahydroisoquinoline and 2-chloro-2'-methyl-6'-methoxy-N-(isopropoxymethyl)acetanilide.

37. A combination comprising: 2-(dichloroacetyl)-1,3-dimethyl-1,2,3,4-tetrahydroisoquinoline and 2-chloro-2',6'-dimethyl-N-(1-pyrazol-1-ylmethyl)acetanilide.

38. A combination comprising: 2-(dichloroacetyl)-1,3-dimethyl-1,2,3,4-tetrahydroisoquinoline and 2-chloro-2'-methyl-6'-trifluoromethyl-N-(ethoxymethyl)acetanilide.

39. A combination comprising: 2-(dichloroacetyl)-1,3-dimethyl-1,2,3,4-tetrahydroisoquinoline and 2-chloro-N-isopropyl-1-(3,5,5-trimethylcyclohexen-1-yl)acetamide.

40. A combination comprising: 2-(dichloroacetyl)-1-ethyl-3-methyl-1,2,3,4-tetrahydroisoquinoline and 2-chloro-2',6'-diethyl-N-(methoxymethyl)acetanilide.

41. A combination comprising: 2-(dichloroacetyl)-1-ethyl-3-methyl-1,2,3,4-tetrahydroisoquinoline and 2-chloro-N-(ethoxymethyl)-6'-ethyl-o-acetotoluidide.

42. A combination comprising: 2-(dichloroacetyl)-1-ethyl-3-methyl-1 2,3,4-tetrahydroisoquinoline and 2-chloro-N-(2-methoxy-1-methylethyl)-6'-ethyl-o-acetotoluidide.

43. A combination comprising: 2-(dichloroacetyl)-1-ethyl-3-methyl-1,2,3,4-tetrahydroisoquinoline and 2-chloro-2'-methyl-6'-methoxy-N-(isopropoxymethyl)acetanilide.

44. A combination comprising: 2-(dichloroacetyl)-1-ethyl-3-methyl-1,2,3,4-tetrahydroisoquinoline and 2-chloro-2',6'-dimethyl-N-(1-pyrazol-1-ylmethyl)acetanilide.

45. A combination comprising: 2-(dichloroacetyl)-1-ethyl-3-methyl-1,2,3,4-tetrahydroisoquinoline and 2-chloro-2'-methyl-6'-trifluoromethyl-N-(ethoxymethyl)acetanilide.

46. A combination comprising: 2-(dichloroacetyl)-1-ethyl-3-methyl-1,2,3,4-tetrahydroisoquinoline and 2-chloro-N-isopropyl-1-(3,5,5-trimethylcyclohexen-1-yl)acetamide.

* * * * *